US00PP26522P3

(12) United States Plant Patent
Spek

(10) Patent No.: US PP26,522 P3
(45) Date of Patent: Mar. 22, 2016

(54) HYBRID ROSE PLANT NAMED 'SPESALLE'

(50) Latin Name: ***Rosa* hybrid**
Varietal Denomination: SPESALLE

(71) Applicant: SPEK ROSE BREEDING INTERNATIONAL B.V., Boskoop (NL)

(72) Inventor: Erik Spek, Boskoop (NL)

(73) Assignee: Spek Rose Breeding International B.V., Boskoop (NL)

( * ) Notice: Subject to any disclaimer, the term of this patent is extended or adjusted under 35 U.S.C. 154(b) by 63 days.

(21) Appl. No.: 13/987,728

(22) Filed: Aug. 26, 2013

(65) Prior Publication Data

US 2015/0059028 P1 Feb. 26, 2015

(51) Int. Cl.
*A01H 5/02* (2006.01)

(52) U.S. Cl.
USPC ..... Plt./139
CPC ..... *A01H 5/0222* (2013.01)

(58) Field of Classification Search
USPC ..... Plt./108, 115, 122, 129, 139, 150, 140
See application file for complete search history.

(56) References Cited

PUBLICATIONS

UPOV International Union for the Protection of New Varieties of Plants for Rose: Guidelines for the Conduct of Tests for Distinctness, Uniformity and Stability, Mar. 24, 2010.*

* cited by examiner

*Primary Examiner* — Anne Grunberg
(74) *Attorney, Agent, or Firm* — Foley & Lardner LLP

(57) ABSTRACT

A new and distinct variety of hybrid rose plant named 'SPESALLE' characterized by an attractive red flower with sufficient stem length, disease resistance, and acceptable productivity for the production of commercial cut flowers. 'SPESALLE' is characterized by a large flower with deep colored, velvety textured red petals in a very regular spiral pattern. The center petals are at the same height with the petals farther away from the center of the flower tapering down from the relatively flat time. The foliage is a dark, glossy green with a shape similar the lemon leaves.

5 Drawing Sheets

Latin name of the genus and species of the plant claimed: *Rosa* hybrid Hybrid Tea Rose.

Variety denomination: 'SPESALLE'.

BACKGROUND OF THE INVENTION

The present invention relates to a new and distinct Hybrid Tea cultivar of Rose plant, botanically known as *Rosa* hybrid, hereinafter referred to by the cultivar name 'SPESALLE'.

The new Hybrid Tea Rose 'SPESALLE' is a product of a breeding program conducted by the inventor, Erik Spek, in Boskoop, The Netherlands. Asexual reproduction of the new hybrid rose 'SPESALLE' is generally performed by grafting, although it can be grown on its own roots. Propagation through patch budding has demonstrated that the combination of characteristics as herein disclosed for the new cultivar are firmly fixed and retained through successive generations of asexual reproduction. The new cultivar reproduces true-to-type.

The new cultivar is produced from the cross of two unpatented, proprietary red seedlings, breeder code '245' as the female parent and breeder code '301' as the male parent.

Initial seed germination and asexual reproduction of the claimed variety 'SPESALLE' took place in Boskoop, The Netherlands, in a climate-controlled greenhouse. After the initial asexual reproduction, plants were selected and shipped to a test facility in Valle de los Chillos, Ecuador for further asexual reproduction and final selection under more typical commercial growing conditions near the equator.

As the variety is genetically stable, the genotype of 'SPESALLE' plants is identical when grown in The Netherlands or in Ecuador, however there is variation in the phenotype due to the difference in climactic conditions. Therefore, the final asexual reproduction and selection of 'SPESALLE' plants occurred in Valle de los Chillos, Ecuador, and commercial production of 'SPESALLE' plants occurs in Cayambe, Ecuador. Data presented in the current application is taken from plants produced under commercial growing conditions in Valle de los Chillos, Ecuador and Cayambe, Ecuador.

BRIEF DESCRIPTION OF THE PHOTOGRAPHS

The accompanying photographs illustrate the overall appearance of the new hybrid rose 'SPESALLE' showing the colors as true as is reasonably possible with colored reproductions of this type. Colors in the photograph may differ slightly from the color values cited in the detailed botanical description which accurately describes the color of 'SPESALLE'.

As shown in the photographs, 'SPESALLE' is characterized by a large flower with deep colored, velvety textured red petals in a very regular spiral pattern. The center petals are at the same height with the petals farther away from the center of the flower tapering down from the relatively flat time. The foliage is a dark, glossy green with a shape similar the lemon leaves.

DETAILED BOTANICAL DESCRIPTION

Figure 1:
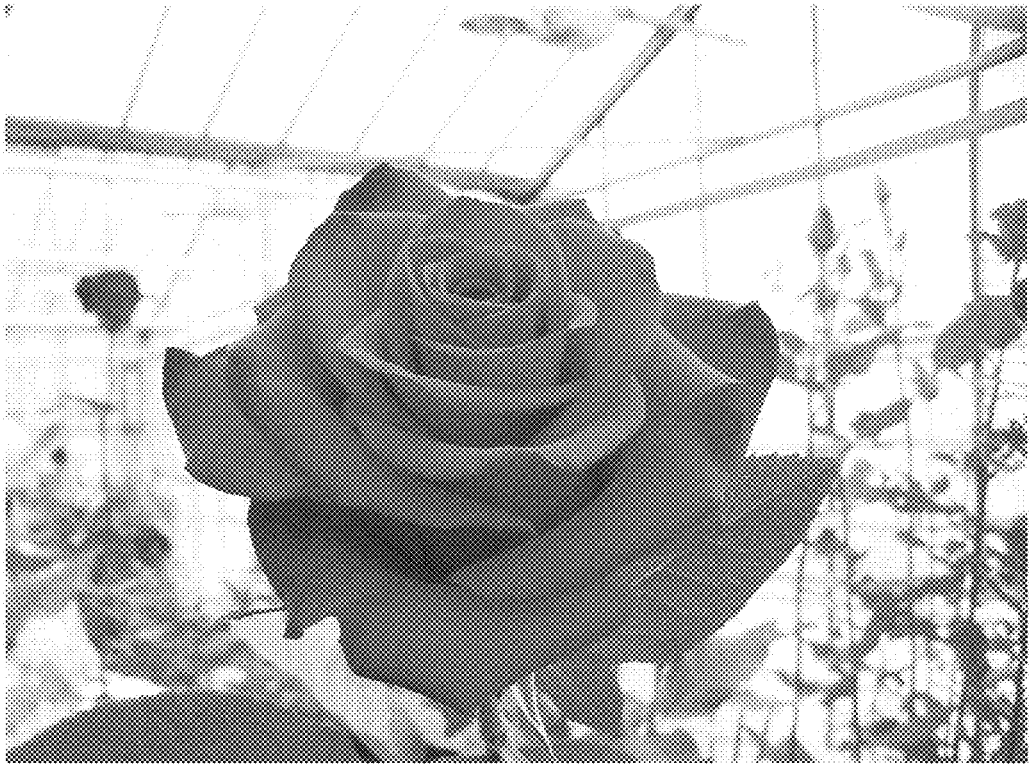
FIG. 1 shows a partially open flower 'SPESALLE' on the plant.
Figure 2:
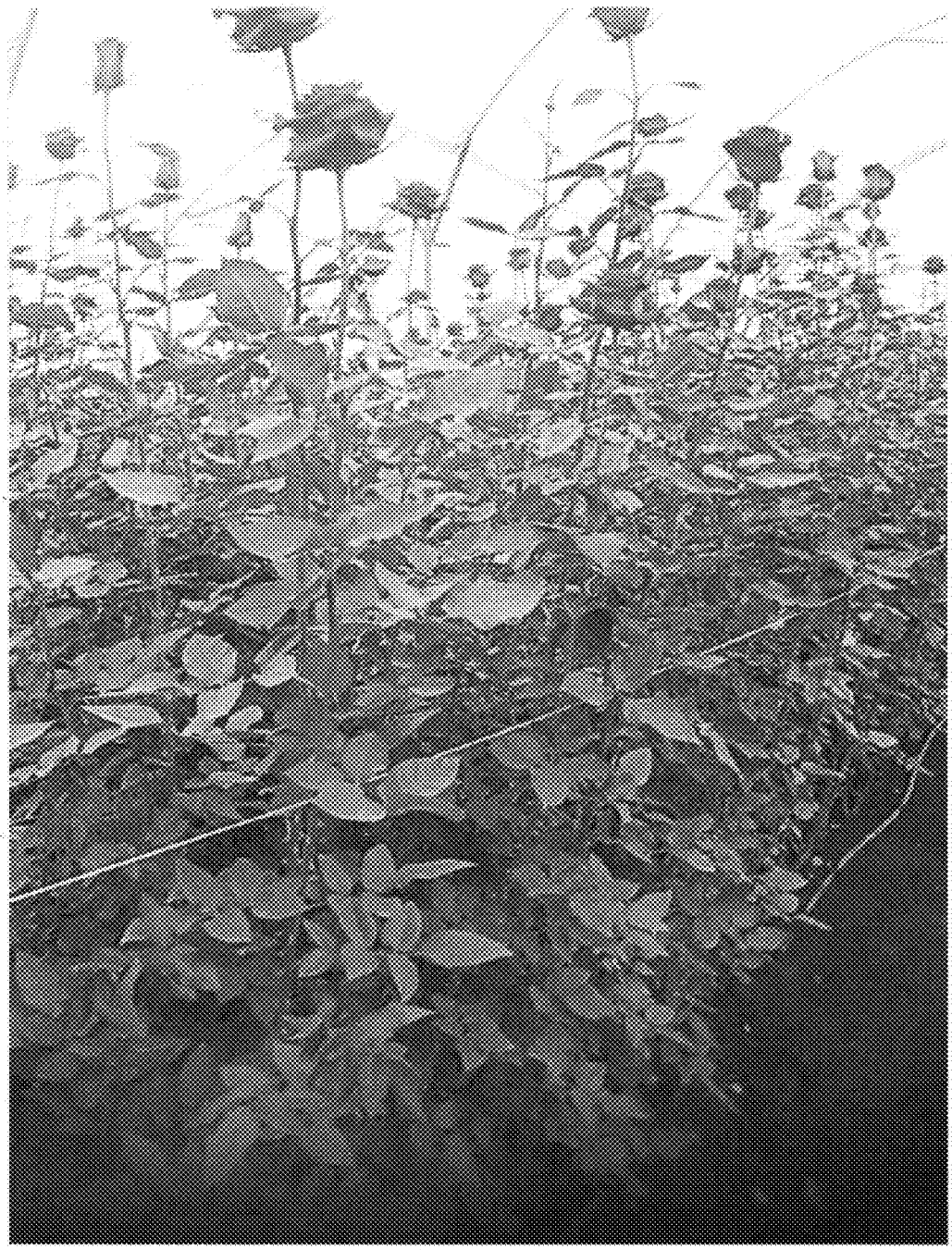
FIG. 2 shows upright growth habit of 'SPESALLE.'
Figure 3:
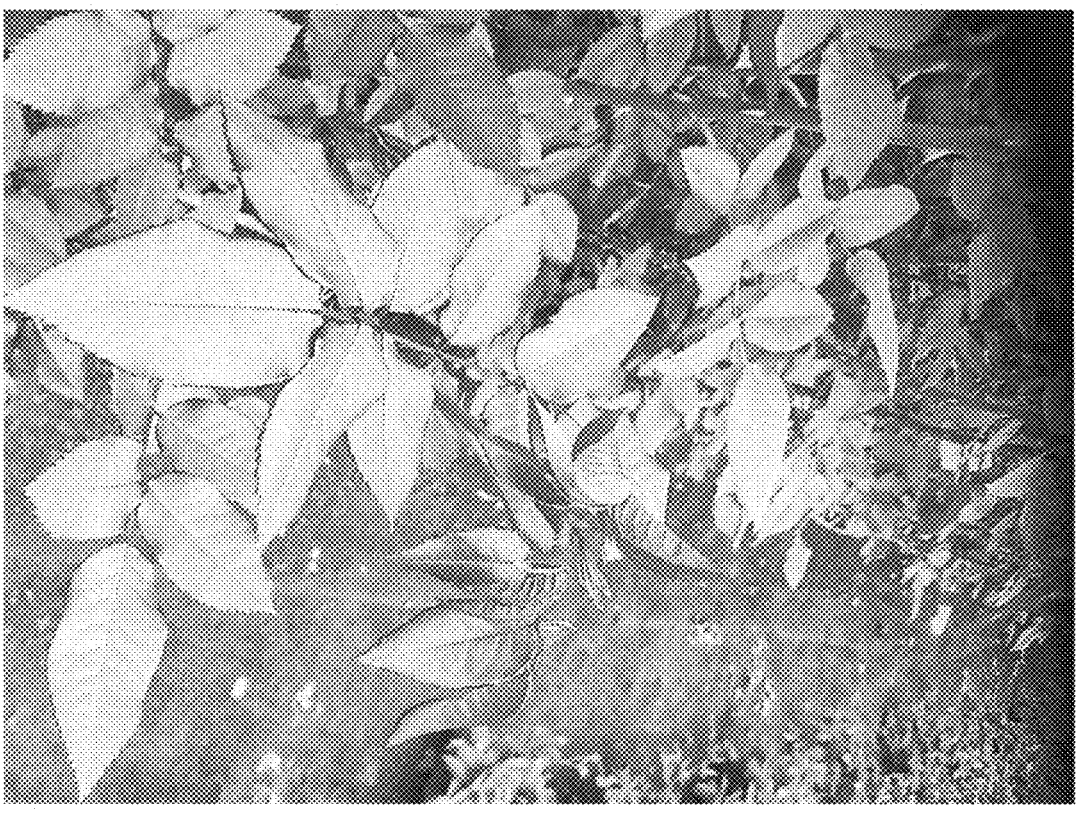
FIG. 3 shows the color and shape of young foliage growth on 'SPESALLE' plants in contrast with mature leaves on the 'SPESALLE' plants.
Figure 4:
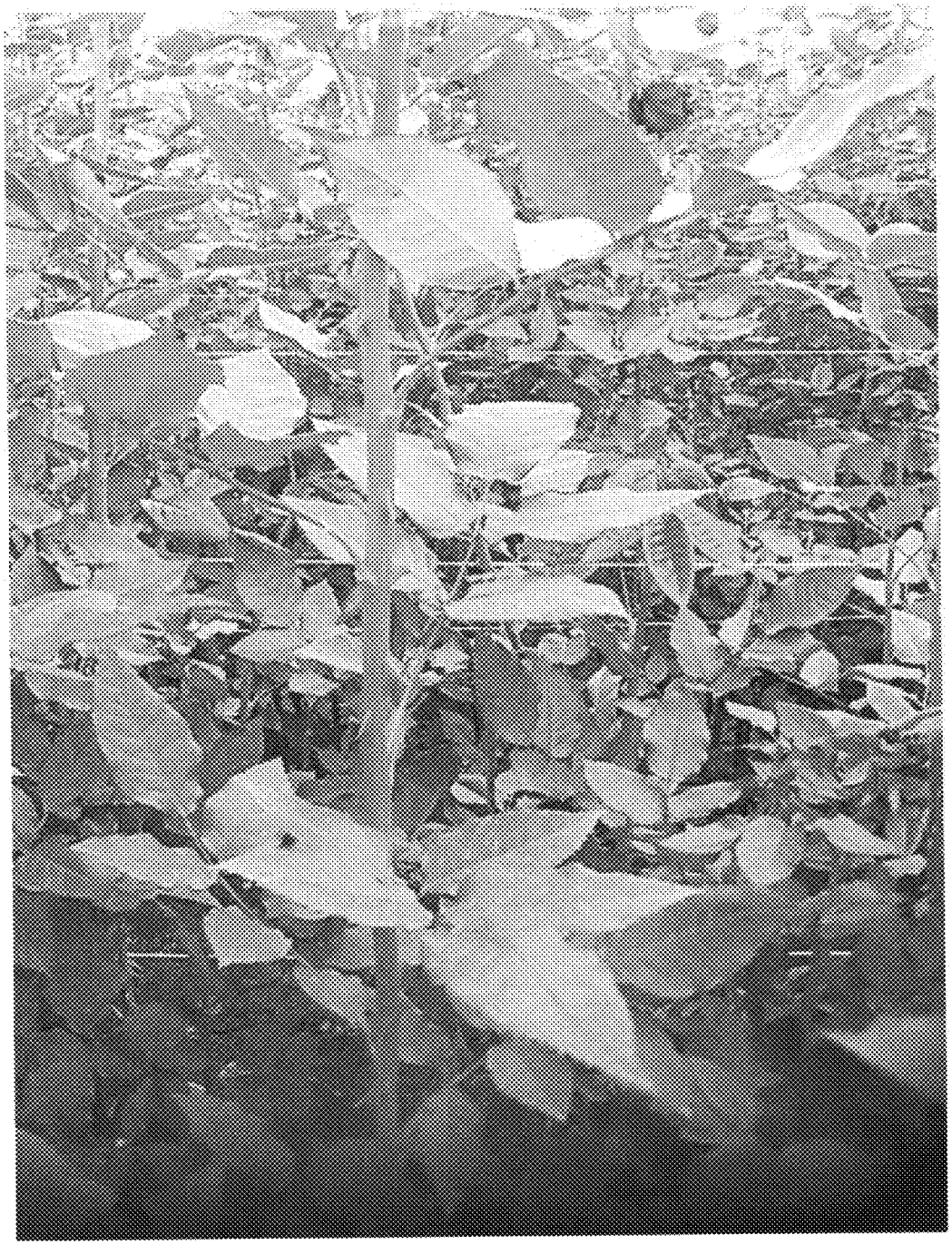
FIG. 4 shows the characteristics of the thorns and stem on the lower part of a stem on 'SPESALLE'
Figure 5:
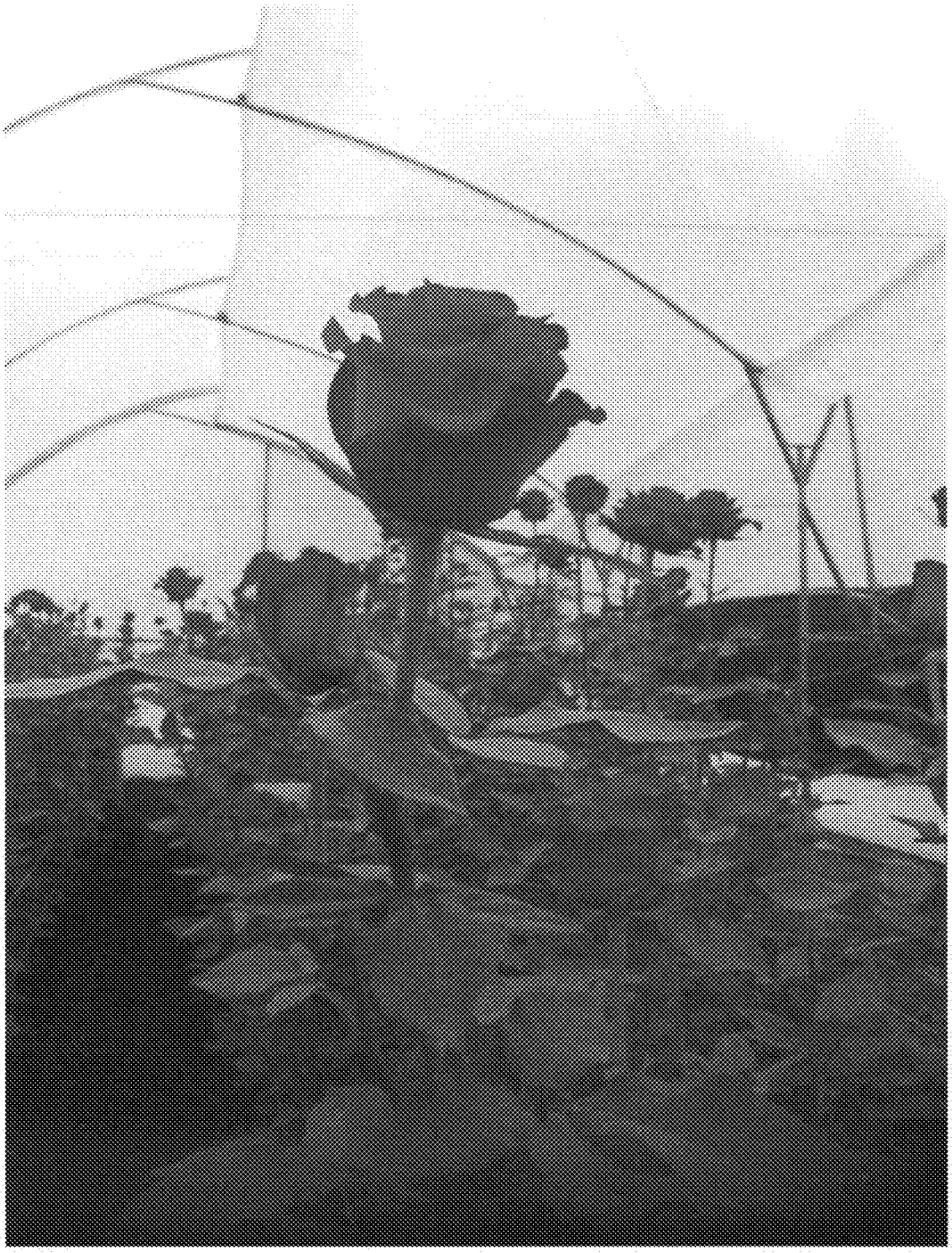
FIG. 5 shows flowers of 'SPESALLE' at various opening stages while still on the plants.

Plants of the cultivar 'SPESALLE' have not been observed under all possible environmental conditions. The phenotype may vary somewhat with variations in environment such as temperature and light intensity which can vary by season, without, however, any variance in genotype. The photographs and following observations and measurements describe plants grown in Valle de los Chillos, Ecuador and Cayambe, Pichincha, Ecuador, under commercial practice in a polyethylene plastic with UV filter covered greenhouse in a climate where the night temperature may drop as low as 2 C but typically reaches about 8 C at night and may rise to around to around 31 C but typically reaches about 21 C day temperatures. The observations are from plants about one year old that were propagated by patch budding on a 'Natal Brier' rose rootstock.

Botanical classification: *Rosa* hybrid Hybrid Tea Rose.

Parentage:

*Female parent*.—Proprietary *Rosa hybrida* selection identified as breeder code number '245', a red seedling.

*Male parent*.—Proprietary *Rosa* hybrid selection identified as breeder code number '301', a red seedling.

Color reference: All color descriptions are based on The Royal Horticultural Society (R.H.S.) Colour Chart, $2^{nd}$ Edition, 1986, published in association with the Flower Council of Holland (PROVORN-ROSSUM).

Comparison varieties: In comparison with the female parent, proprietary seedling number '245', 'SPESALLE' is larger, as the flowers of '245' are approximately 5 cm in the height of the head versus up to 7.5 cm, longer, as cut flowers from the seedling normally have 50 to 70 cm stem lengths while 'SPESALLE' can be much longer. The inner petal color of '245' is RHS Red Group 46 A which is similar to 'SPESALLE'. Both have a symmetrical shape with the petals arranged in a spiral form. In comparison with the male parent, proprietary seedling number '301', the flower head of 'SPESALLE' is approximately the same size but has a regular spiral center, where the male parent '301' has an irregular arrangement of petals in the center. Additionally, the inner petal color of the male parent '301' is slightly lighter (RHS 45A) than the inner petal color of 'SPESALLE' (RHS 46A). In comparison with the similar variety 'Tan97544' (Patented, U.S. Plant Pat. No. 16,697) 'SPESALLE' has a larger flower head, does not have the dip in the center of the flower head, is slightly darker in petal color (RHS Red Group 46 A versus RHS Red Group 45 A) and has more petals.

Propagation: Although the cultivar can be propagated from a rooted cutting, it is recommended that it be budded on a suitable rootstock such as *Rosa hybrida* var. 'Manetti' or 'Natal Brier' for greenhouse production of roses. The grafting can be as a bud, t-graft stentling or other type of graft. The rootstocks for budded plants should generally be grown for several weeks if the grafting is in the greenhouse for the plant to be actively growing to accept the bud.

*Rooting habit*.—Will depend upon the rootstock used.

Plant:

*General appearance*.—The cultivar 'SPESALLE' is a tall, upright, freely branching shrub that will produce both basal breaks and branches from the pinched plants. Although generally grown using a system with posts and wire or string guides, the observed and typical plant growth habit does not require any special treatment to insure a primarily vertical growth habit.

*Plant height, lateral branches, stems and internodes*: Typically, the plant will be managed with flower cutting points between 30 cm and 150 cm. This can result in an overall plant height over 2 meters depending upon plant management. Lateral branches will generally be from 40 cm to up to 150 cm. The normal diameter of the lower area can vary from 0.6 cm to 1.0 cm, in the middle area from 0.6 cm to 0.8 cm, and peduncle diameter from 0.4 cm to 0.6 cm. A typical plant produces 10-14 stems per year. Visual differences in the diameter of stems on the same plant are common. Internode length is generally from 3.0 to 8.0 cm and the stem texture is smooth. The color of the branches approaches RHS Green 137B. Internode length on the stem between leaves is generally around 6 to 7 cm. Young shoots have a strong intensity of anthocyanin coloration which disappears as the stem matures.

*Peduncle*.—Peduncle is green similar to the rest of the stem with a color approaching RHS Green 137B. Peduncle is thornless and free of prickles. The typical length of the peduncle is 6 to 10 cm before coming to at least the first incomplete leaf.

*Plant diameter*.—The plant diameter will generally be managed with a diameter up to 30 cm.

*Thorns*.—Reddish brown color, similar to RHS 165B from the greyed orange group, up to about 35 or 40 cm from the base of the flower. The thorns under normal growing conditions are about 0.5 cm. long. Thorns are generally not present in the upper 40 cm of the stem. Below that point, they are spaced 3 cm to 4 cm apart. At the base the thorns have a length of about 1.8 cm, width of 2 mm and height of 0.6 to 0.8 cm. The thorn shape is very pointed with the tip pointing slightly down.

*Seed/fruit*.—None observed.

*Petioles*.—The petioles are 4 to 6 cm long, have a diameter of 0.15 cm, a smooth texture, a upper surface color RHS Green-White group 157A, and an under surface color similar to Green Group 143A.

*Stipules*.—Stipules of 'SPESALLE' extend out from the base of the petiole approximately two-thirds of the distance to the first pair of leaflets, and at the end of the stipules the stipules have two narrow, pointed, auricles with a total width of approximately 1.5 cm while the stipules have a total width of approximately 0.75 cm. There is only the one single pair of stipules per petiole. The color of the stipules is closest to RHS Green 135A.

*Flower buds*.—The bud shape of flowers at cut point is generally relatively flat at the top with the two outer petals forming rings at progressively lower levels. At a typical cutting point, the flower bud is from 6.5 to 7.5 cm high, 5 to 6 cm wide and has a color near RHS Red 41B.

*Flowers*.—The exact count may vary but the flowers typically have about 33 to 36 petals. The first flowers produced on the plant may have over 50 petals. A flower at cut point may be up to 7.5 cm wide and 7.5 cm high. The inner side of the petals is between RHS Red 41A and 46A and the outer side of the petals and the petals showing at the top of closed flowers near RHS Red 41B. Petal color may darken with age. Slight blackening of petals may be observed depending upon degree of protection against UV radiation during flower production. Flowers do not generally open to the point where the stamens and pistil are visible.

*Fragrance*.—The petals have no noticeable fragrance.

*Petals*.—The edge of the petals is rounded with a slight extension to a rounded tip. The color description is included in the description of the overall flower. The outer petals often have pronounced whitish veins that fan out from the center of the base of the petal. Inner petals have less pronounced veins. Outer petals grown under the conditions of Cayambe, Ecuador have a size of about 5 cm in diameter. Inner petals are slightly larger and more oval with a width of about 6 cm and a length of about 7 cm. The base of the petals is almost rounded.

*Sepals*.—Sepals are narrow near the tip, approximately 4 cm long under normal conditions, with two or three pairs of larger serrations on each side along with some very small serrations near the tip appearing in some sepals. Flowers have five sepals and are 1.75 cm wide at the base and 2.0 cm wide at the widest point. Other sepals may have relatively smooth edges. Color of the sepals is near RHS Green 137A although slight yellowing may appear at the base of the sepals. The texture of the upper surface of the sepals is slightly bristled, while the lower surface is not bristled but the texture is slightly rough.

*Receptacle*.—The base of the receptacle is almost flat and has a color similar to the stem color of RHS Green 137B. The width from the anthers on one side of the flower to the other is about 3 cm with the top of the stigma on top of the pistil protruding nearly 1 cm above the highest point of the stamen. This would be a significant hindrance to self-pollination, which has not been reported under commercial conditions. The receptacle at its widest point is about 1.5 cm on an un-pollinated flower while the total height is about 2 cm.

*Foliage*.—There are four different types of leaves on the typical stem of 'SPESALLE'. Complete leaves and leaflets are large and strongly glossy. The lower leaves may have seven leaflets, with an individual leaflet length of 4 to 9 cm and individual leaflet width of 3 to 4 cm, an overall leaf length of 18 to 22 cm and an overall width of approximately 15 cm, middle leaves generally have five leaflets with an individual leaflet length of 8 to 14 cm and width of 17 to 18 cm, an overall leaf length of 18 to 25 cm, and an overall width of 16 to 20 cm. Upper leaves generally have three leaflets with individual leaflet length of 8 to 13.5 cm and individual leaflet width of up to 7 cm in the center leaflet and 4 cm in the side leaflets, and a total leaf length of 18 to 22 cm and total leaf width of 16 to 18 cm. Widths can be affected by fertilization and environmental conditions. Just below the peduncle it is common to have incomplete leaflets with a length of 5 to 10 cm and a width of about 2 cm. The incomplete leaflets may start at 25 cm from the base of the receptacle. The upper side of leaves have a color between RHS Green 136A and 143A and a lower side of the leaves close to RHS Green 138 A, depending upon leaf age and fertilization of the plant. The glossy foliage with odd pinnate leaves, have ovate leaflets with a serrated edge and a rounded leaf base. The terminal leaflet is acuminate in shape at the tip with a rounded base. Leaf venation color is not different than the leaf colors, other than the central vein being a lighter green, similar to RHS Green 129D.

*Flower longevity*.—Normal vase life after transport is 10 to 12 days, although the flower will generally last several days longer on the plant.

*Disease and pest resistance*.—Normal, with some susceptibility to *Botrytis cinerea*.

*Physiological disorders*.—When grown under certain climatic conditions or with an inadequate proportion of Calcium to Potassium, slight bronzing may be observed in the color of the petals.

*Reproductive organs*.—Filament: Number: 40 to 50 per stem; Length: 1.5 to 2.5 cm; Diameter: Approx. 0.25 cm; Color: RHS 46A Red. Anther: Number: One per stem; Length: 4 mm; Width: 1.5 mm; Color: RHS 23C Yellow-Orange. Ovary: Number: One per stem; Width: 3-4 cm; Height: 1-2 cm; Color: RHS 164C Greyed-Orange; Shape: Pitcher-shaped in longitudinal section. Style: Number: One per stem; Length: 1 to 1.5 cm; Diameter: Approx. 0.25 cm; Stigma color: RHS 42B Red.

If the whole set of reproductive organs is allowed to dry on the plant, the color browns to between RHS165B and RHS165C, Greyed-Orange. 'SPESALLE' flowers have not been observed to self-pollinate, perhaps due to the pistil being higher than the stamen which would hinder transfer of pollen to the top of the stigma from the anthers. A rose hip would be produced if the flower were allowed to pollinate and the fruit were allowed to form.

What is claimed is:

1. A new and distinct variety of rose plant named 'SPESALLE', as herein illustrated and described by the characteristics set forth above.

* * * * *